United States Patent
Hall et al.

(10) Patent No.: US 10,165,980 B2
(45) Date of Patent: Jan. 1, 2019

(54) TOILET WITH A HEALTH MONITORING TORSO BELT

(71) Applicants: David R. Hall, Provo, UT (US); Dan Allen, Springville, UT (US); Ben Swenson, Lehi, UT (US); Huntington Tracy Hall, Provo, UT (US); Joe Fox, Spanish Fork, UT (US)

(72) Inventors: David R. Hall, Provo, UT (US); Dan Allen, Springville, UT (US); Ben Swenson, Lehi, UT (US); Huntington Tracy Hall, Provo, UT (US); Joe Fox, Spanish Fork, UT (US)

( * ) Notice: Subject to any disclaimer, the term of this patent is extended or adjusted under 35 U.S.C. 154(b) by 202 days.

(21) Appl. No.: 15/196,321

(22) Filed: Jun. 29, 2016

(65) Prior Publication Data
US 2018/0000417 A1    Jan. 4, 2018

(51) Int. Cl.
| A61B 5/00 | (2006.01) |
|---|---|
| A61N 1/04 | (2006.01) |
| A61B 5/08 | (2006.01) |
| A61B 5/053 | (2006.01) |
| A61B 5/0408 | (2006.01) |
| A61B 5/024 | (2006.01) |
| A61B 5/0205 | (2006.01) |
| A61B 8/00 | (2006.01) |
| A61B 7/02 | (2006.01) |
| E03D 11/00 | (2006.01) |

(Continued)

(52) U.S. Cl.
CPC ............ *A61B 5/6823* (2013.01); *A47K 13/24* (2013.01); *A61B 5/024* (2013.01); *A61B 5/04085* (2013.01); *A61B 5/0816* (2013.01); *A61B 5/6831* (2013.01); *A61B 5/6887* (2013.01); *A61B 5/6891* (2013.01); *A61B 7/02* (2013.01); *A61B 7/04* (2013.01); *A61B 8/0883* (2013.01); *A61B 8/4227* (2013.01); *A61N 1/046* (2013.01); *A61N 1/3904* (2017.08); *A61N 1/3993* (2013.01); *A61B 8/40* (2013.01)

(58) Field of Classification Search
None
See application file for complete search history.

(56) References Cited

U.S. PATENT DOCUMENTS

| 2,249,322 | A | * | 7/1941 | McQuaid ............... | A47K 13/06 4/239 |
|---|---|---|---|---|---|
| 4,819,278 | A | * | 4/1989 | Ramos .................. | A47K 17/02 280/304.1 |

(Continued)

*Primary Examiner* — Brian T Gedeon (57) ABSTRACT

A toilet torso belt with sensors is disclosed. The torso belt is used by a toilet user while the toilet user is using the toilet to take health measurement readings of the user. Dynamic heart stress readings may be obtained and monitored over weeks, months and years. Rolling averages of heart function and heart health may be determined and deviations from the rolling averages may trigger notifications. Other health related measurements and functions such as temperature, respirations, heart rate, electrocardiogram, echocardiogram, and stethoscope sounds are also recorded and stored for trending and data analysis. An adjustable tensioner compresses the torso belt against the user's torso with a sufficient force based on the user's height, weight, sex, and age, and whether the sensors are against the user's skin or clothing, to allow the sensors to take measurements of the user.

18 Claims, 8 Drawing Sheets

(51) Int. Cl.
*A47K 13/24* (2006.01)
*A61B 7/04* (2006.01)
*A61N 1/39* (2006.01)
*A61B 8/08* (2006.01)

(56) References Cited

U.S. PATENT DOCUMENTS

| | | | | |
|---|---|---|---|---|
| 5,492,285 A * | 2/1996 | Hamrick | ............... | A61F 5/04 |
| | | | | 128/876 |
| 5,738,112 A * | 4/1998 | Brod | ............... | A47K 17/02 |
| | | | | 128/869 |
| 5,945,914 A * | 8/1999 | Holmes | ............... | G08B 21/22 |
| | | | | 200/85 A |
| 6,112,337 A * | 9/2000 | Brod | ............... | A47K 17/02 |
| | | | | 4/254 |
| 6,524,239 B1 * | 2/2003 | Reed | ............... | A61B 5/0002 |
| | | | | 128/920 |
| 6,603,999 B2 * | 8/2003 | SerVaas | ............... | A61N 1/39 |
| | | | | 607/5 |
| 6,775,902 B1 * | 8/2004 | Huai | ............... | G11B 5/31 |
| | | | | 216/22 |
| 8,747,336 B2 * | 6/2014 | Tran | ............... | G06F 19/3418 |
| | | | | 600/587 |
| 9,751,534 B2 * | 9/2017 | Fung | ............... | G06F 19/345 |
| 2007/0293781 A1 * | 12/2007 | Sims | ............... | A61B 5/1135 |
| | | | | 600/534 |
| 2015/0119679 A1 * | 4/2015 | Huang | ............... | A61B 5/1072 |
| | | | | 600/407 |
| 2017/0296833 A1 * | 10/2017 | Jaax | ............... | A61N 1/3787 |

\* cited by examiner

TOILET WITH A HEALTH MONITORING TORSO BELT

BACKGROUND

Field of the Invention

This invention relates to medical toilets for taking health measurements of a user while using a toilet.

Background of the Invention

Using a toilet is for some the hardest work they will do in the course of a day. The toilet is dynamically useful for obtaining health-related measurements because of its frequency of use and because of the exertion required to relieve a body of waste. Toilets are used in a private location with frequent user body contact. Torso measurements for health include stethoscope, EKG, and echocardiogram. However, known toilets do not provide access to a user's torso, only the back side of a user and the back of their legs.

SUMMARY

A toilet torso belt with sensors is disclosed. The torso belt is used by a toilet user while the toilet user is using the toilet to take health measurement readings of the user. Dynamic heart stress readings may be obtained and monitored over weeks, months and years. Rolling averages of heart function and heart health may be determined and deviations from the rolling averages may trigger notifications. Other health related measurements and functions such as temperature, respirations, heart rate, electrocardiogram, echocardiogram, and stethoscope sounds are also recorded and stored for trending and data analysis.

A belt arrangement places electrodes close to the heart which is in the center left of the torso and aligns with the main polarization wave of the heart which has an axis from the upper right to the lower left of the body, centered on the heart and lungs. The present invention provides a toilet with a torso strap or belt. The belt has sensors on it for measuring health. Users can strap the belt across their torso for example from their shoulder to their opposite hip, or across their torso and under both armpits. The belt may have a height adjustment mechanism to compensate for users of different height. The height adjustment can be done automatically via a motorized actuator based on a measured height or user profile or set manually. The belt may have an auto-tensioner. The tensioner may be a variable tensioner, adjustable for the height, weight, sex, and age of the user. The tensioner may provide sufficient force against the torso of the user while the user is using the toilet to allow the sensors to measure the user. A sufficient force is in the range of about 2.5 N to 35 N per linear belt inch. The force required may vary depending on the particular sensors selected by the user and on the height, weight, sex, and age of the user, and whether the sensors are placed directly against the user's skin or are placed on the user's clothing. The tensioner may comprise an elastomer or coil spring providing a positive connection force for the torso sensors and optionally holding a user's back steady against the turned up lid of the toilet, which may have additional sensors such as microphones to listen for lung congestion. Sensors can include an ultrasound imager used in echocardiograms. Sensors can include a stethoscope or microphone. Sensors may include electrode sensors, microphone sensors, acoustic sensors, ultrasound sensors, motion sensors, strain sensors, optical sensors, temperature sensors, electrocardiogram (ECG or EKG) sensors, and/or stethoscope sensors. Strain sensors, motion sensors, or sound sensors may be used to detect an elimination event.

The user may operate the torso belt to obtain personal measurements or be instructed to do so by a directing health care professional or mobile device application when advisable.

Frontal body EKG measurements have standard electrode placement locations for diagnostic EKG purposes. These provide additional information over what can be obtained from a hand-to-hand EKG measurement. Additionally, because a toilet provides contact with the thigh, a driven-right-leg EKG electrode can be provided in the toilet seat. Driven right leg has benefits for obtaining a higher quality EKG signal by controlling the body potential relative to the sensor.

In an example the user connects the belt at their hip and the toilet moves the belt connection point higher from the hip upwards toward the left armpit to wrap the belt around the heart region, then returns to the original position for ease of removal after the measurement is complete. In another example, the belt is provided with a defibrillator for a remote, physician-supervised cardio vert procedure, or an automated external defibrillator (AED) for emergency use. A stethoscope or multiple stethoscopes—basically microphones in contact with the body—attached to the belt can measure the sound of heart valves and blood flow.

A toilet provides many benefits over a standard seat for taking health measurements. For example, a toilet provides a private location where a user may remove his or her shirt for obtaining direct skin contact sensor readings. Additionally, a toilet is used multiple time a day prompting routine data collection compared to sitting on a chair or other object which a user may forget to do. A toilet also provides a natural stress on the heart while passing waste into the toilet enabling dynamic sensor data indicative of heart problems and blood flow problems.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which.

DETAILED DESCRIPTION

It will be readily understood that the components of the present invention, as generally described and illustrated in the Figures herein, may be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings.

Figure 1:
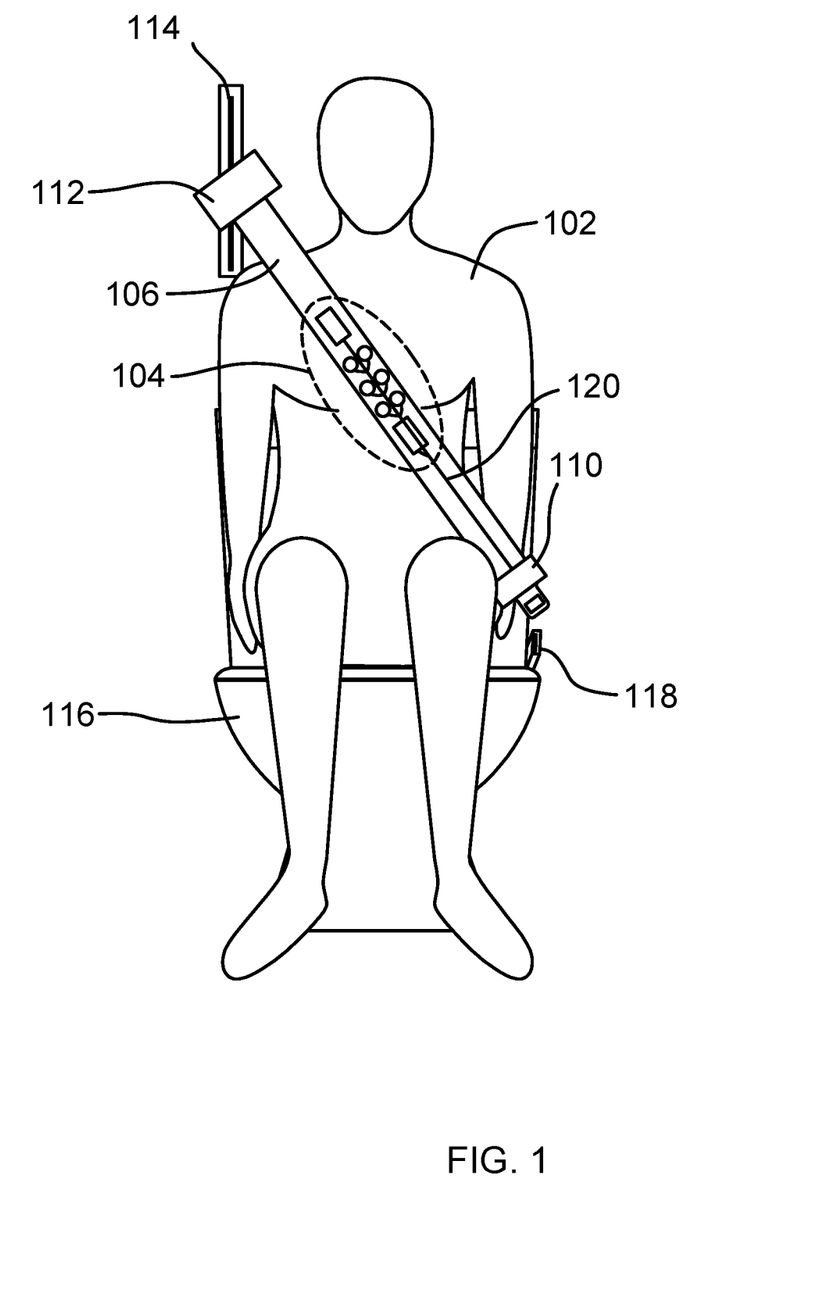
FIG. 1 is a front view of a toilet user sitting on a toilet with a diagonal torso belt in accordance with an embodiment of the invention.

FIG. 1 shows a toilet user 102 sitting on a toilet 116 with a torso belt 106 diagonally pulled across the user's torso. Torso belt 106 contains one or more sensors 104 for measuring the user while the user is sitting on the toilet or while the user is using the toilet. The sensors 104 may comprise electrode sensors, microphone sensors, acoustic sensors, ultrasound sensors, motion sensors, strain sensors, optical sensors, temperature sensors, electrocardiogram (ECG or EKG) sensors, and stethoscope sensors. The sensors may receive data for determining a user's temperature, respirations, heart rate, electrocardiogram, echocardiogram, and stethoscope sounds. A controller may be coupled to the sensors and programed to determine one or more of: a user's temperature, respirations, heart rate, electrocardiogram, echocardiogram, and stethoscope sounds from the data received from the one or more sensors in the torso belt. The sensors 104 may have wires 120 which run along the torso belt or which are imbedded within the torso belt. The wires may connect to a wireless controller located within buckle 110. The wireless controller may process and communicate signals obtained from sensors 104 to a remote location such as a server or computer. Buckle 110 may be received by a receiving buckle 118 which is connected to toilet 116. Alternatively, the wires 120 may run along the torso belt in the opposite direction toward belt end 112. Belt end 112 may contain a wireless controller for receiving and transmitting signals obtained by sensors 104. Sensors 104 may obtain health data of a user while a user is sitting on the toilet or while a user is using the toilet. Health data may be more beneficial when it is obtained while a user is bearing down on a toilet while passing waste into the toilet. For example, a user's heart rate and ECG readings before, after, and while bearing down to pass waste may provide dynamic heart strain data. This information may be useful in monitoring a user's heart health condition over time and providing an early diagnosis of one or more heart conditions of a user. Similar type health measurements and health determinations may be made in relation to respirations of a user, temperature of a user, blood flow of a user, heart rhythm of a user, heart valve conditions of a user, blood flow through arteries and veins of a user, and bronchial inflammation of a user. The health measurement data may be archived and stored in an online user library health data system. The stored data may be used to preform data analysis on sets of data relating to changes over time in user health trends and user health conditions. Neuro-networks may be trained and learn significant trends relating to data sets of each sensor and to correlations among data sets of one or more sensors. A height adjustment mechanism 114 may enable the torso belt 106 to be adjusted along a height of a user. Torso belt 106 may contain an automatic tensioner located near an end of the belt 112. The tensioner may provide a variable force against the user based on the user's height, weight, sex, and age. The tensioner may provide sufficient force against the torso of the user while the user is using the toilet to allow the sensors to measure the user. A sufficient force is in the range of about 2.5 N to 35 N per linear belt inch. The force required may vary depending on the particular sensors selected by the user and for the height, weight, sex, and age of the user, and whether the sensors are placed directly against the user's skin or are placed on the user's clothing. Such a tensioner system may be a spring tensioner or rotational tensioner. The tensioner may help to retract the belt 106 against a user's torso 102 allowing sensors 104 to be adjacent to or properly positioned for taking measurements of a user using or sitting on toilet 116. The tensioner may be motorized or spring loaded. When a user sits on a toilet the user may be tactilely stimulated or audibly reminded to use the torso belt. Tactile stimulation or audile feedback may be given when the torso belt is properly positioned and tensioned.

A user 102 may be using toilet 116 while sensors 104 are monitoring the user's heart. While the user 102 is bearing down to eliminate waste, the user's heart may start into atrial fibrillation. A toilet controller associated with the sensors detects the atrial fibrillation and informs the user that heart defibrillation is necessary. The user may or may not acknowledge and confirm or override defibrillation. The toilet controller may then initiate a discharge current to electrodes on the torso belt for a controlled time and power output to reset an irregular heartbeat of the user. The toilet controller may inform the user of a successful defibrillation. The controller may also direct the user to lean forward to apply pressure to the belt if the electrodes are not making good contact with a torso of the user. An automatic torso belt tensioner may increase tension in the torso belt to obtain good contact between skin of the user and sensors on the torso belt. Torso belt sensor readings may provide feedback to a toilet controller and user about a connection or interface status of the torso belt sensors to the user's skin. A user may be able to reposition the belt or tighten the belt to achieve an acceptable sensor interface. One or more sensors may be used to determine an elimination event of a user using the toilet. For example, a motion sensor or a strain sensor may detect tightening of torso muscles of a toilet user or a microphone or stethoscope may detect a user holding his or her breath while bearing down during an elimination processes. Detection on an elimination process may trigger one or more data collection systems to retrieve or correlated data that is collected from the user. An elimination event may provide a reference point in data correlation and aggregation.

Figure 2:
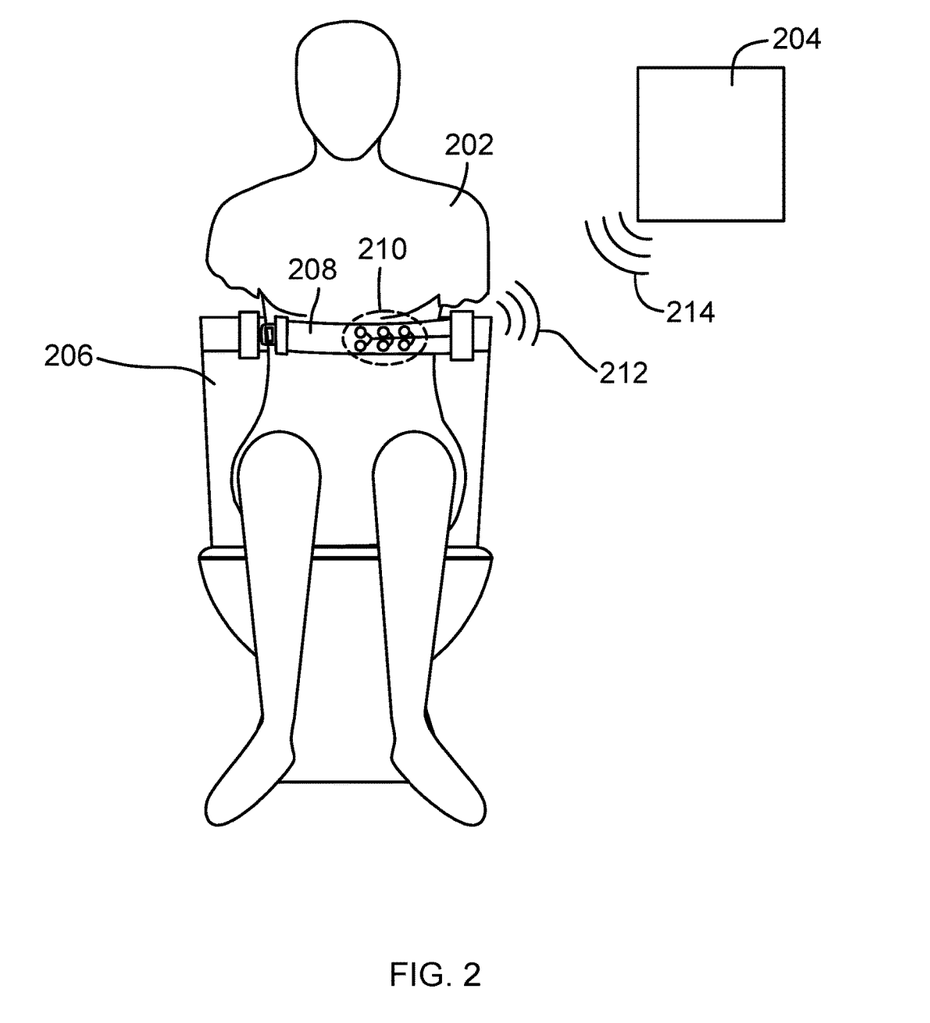
FIG. 2 is a front view of a toilet user sitting on a toilet with a horizontal torso belt in accordance with an embodiment of the invention.

In FIG. 2, a user 202 is sitting on toilet 206 with a horizontal torso belt 208 horizontally stretched across the torso of user 202. The torso belt 208 contains one or more sensors 210. The sensors 210 may comprise one or more of: electrode sensors, microphone sensors, acoustic sensors, ultrasound sensors, motion sensors, strain sensors, optical sensors, temperature sensors, electrocardiogram (ECG or EKG) sensors, and/or stethoscope sensors. The sensors 210 may have wires which run along the torso belt or which are imbedded within the torso belt. The wires may connect to a wireless controller located within the toilet 206. The sensors may receive data for determining a user's temperature, respirations, heart rate, electrocardiogram, echocardiogram, and stethoscope sounds. A controller may be coupled to the sensors and programed to determine one or more of: a user's temperature, respirations, heart rate, electrocardiogram, echocardiogram, and stethoscope sounds from the data received from the one or more sensors in the torso belt. The wireless controller may process and communicate signals 212 obtained from sensors 210 to a remote location such as a server or computer 204. Torso belt 208 may be connected to a tank 206 of the toilet. Sensors 210 may disposable or removable sensors or have removable interfaces which couple the sensors to a user's skin or body. The removable interfaces may be ECG or EKG electrodes or other disposable sensor interfaces which provide coupling and sanitary conditions for the user.

Figure 3:
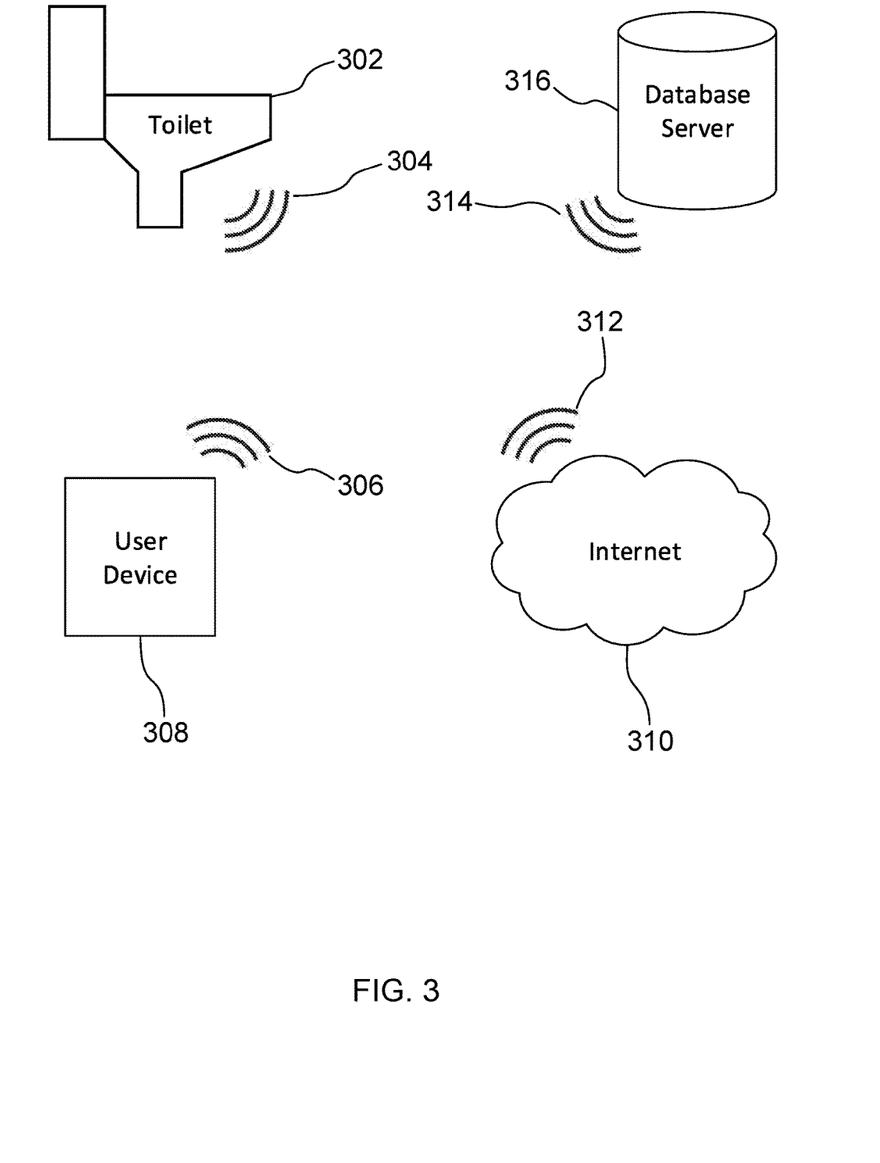
FIG. 3 a diagram showing communications between a toilet and a network in accordance with an embodiment of the invention.

In FIG. 3, a toilet 302 is able to communicate data signals to a user device 308 or to a database server 316 or to another Internet location such as a website or network address. Communication signals 304, 306, 312, and 314 may be WiFi signals, Sure-Fi signals, Bluetooth signals, near field communication signals, cellular radio signals, or a combination thereof. Toilet 302 may have a controller for gathering and transmitting health data of a user using the toilet. The health data may be gathered by means of sensors in a torso belt, toilet seat sensors, toilet foot sensors, and/or any combination thereof. The data may be transmitted and stored in a remote database 316, in a user device 308, or another network address of a computer or webserver. The user device may be a smart phone or tablet device.

Figure 4:
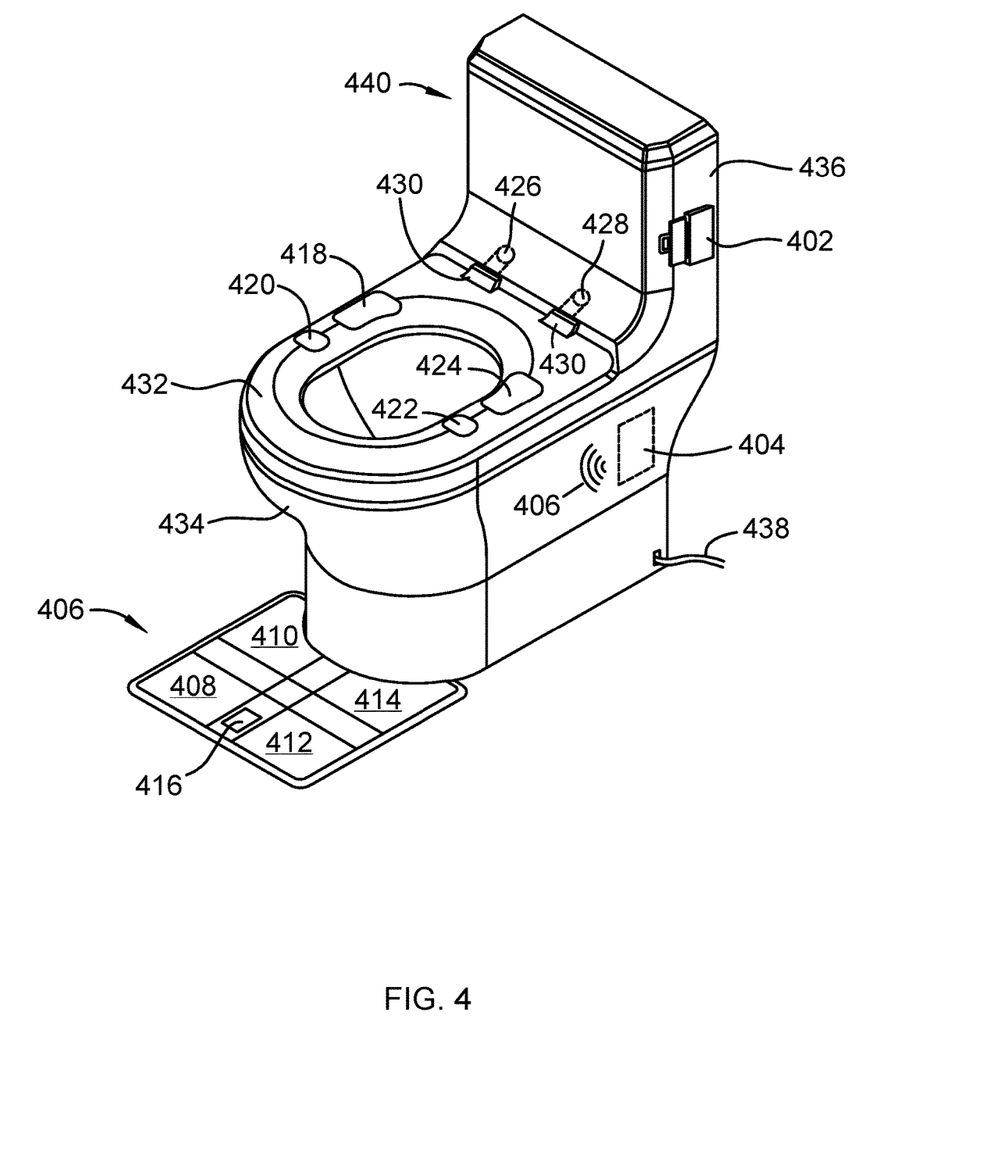
FIG. 4 is an isometric view of a toilet with a horizontal torso belt in accordance with an embodiment of the invention.

In FIG. 4, a toilet 440 is shown with sensors 420, 418, 422, and 424 on toilet seat 432. The toilet seat sensors 420, 418, 422, and 424 may be used in combination with torso belt sensors to determine health data measurements of a user. Toilet foot sensors 410, 408, 412, and 414 may be used in combination with toilet seat sensors 420, 418, 422, and 424, and/or with torso belt sensors to determine bio-impedance health data measurements of a user. A toilet controller 404 may provide a processor and transceiver for processing sensor data and communicating the sensor data to a remote computer. Controller 404 may communicate wirelessly or by wire to other computer or network devices. Torso belt 402 is a horizontal torso belt which is stretches across a user while the user is using toilet 440. Toilet 440 also may include strain sensors 426 and 428 for determining a weight of a user. Strain sensors 426 and 428 may be used in combination with strain sensors located within foot scale device 406 to determine an overall weight of a toilet user. Torso belt 402 may stretch across a user while the user is sitting on the toilet base 434 and the torso belt may connect to a receiving buckle on an opposite side of tank 436.

Figure 5:
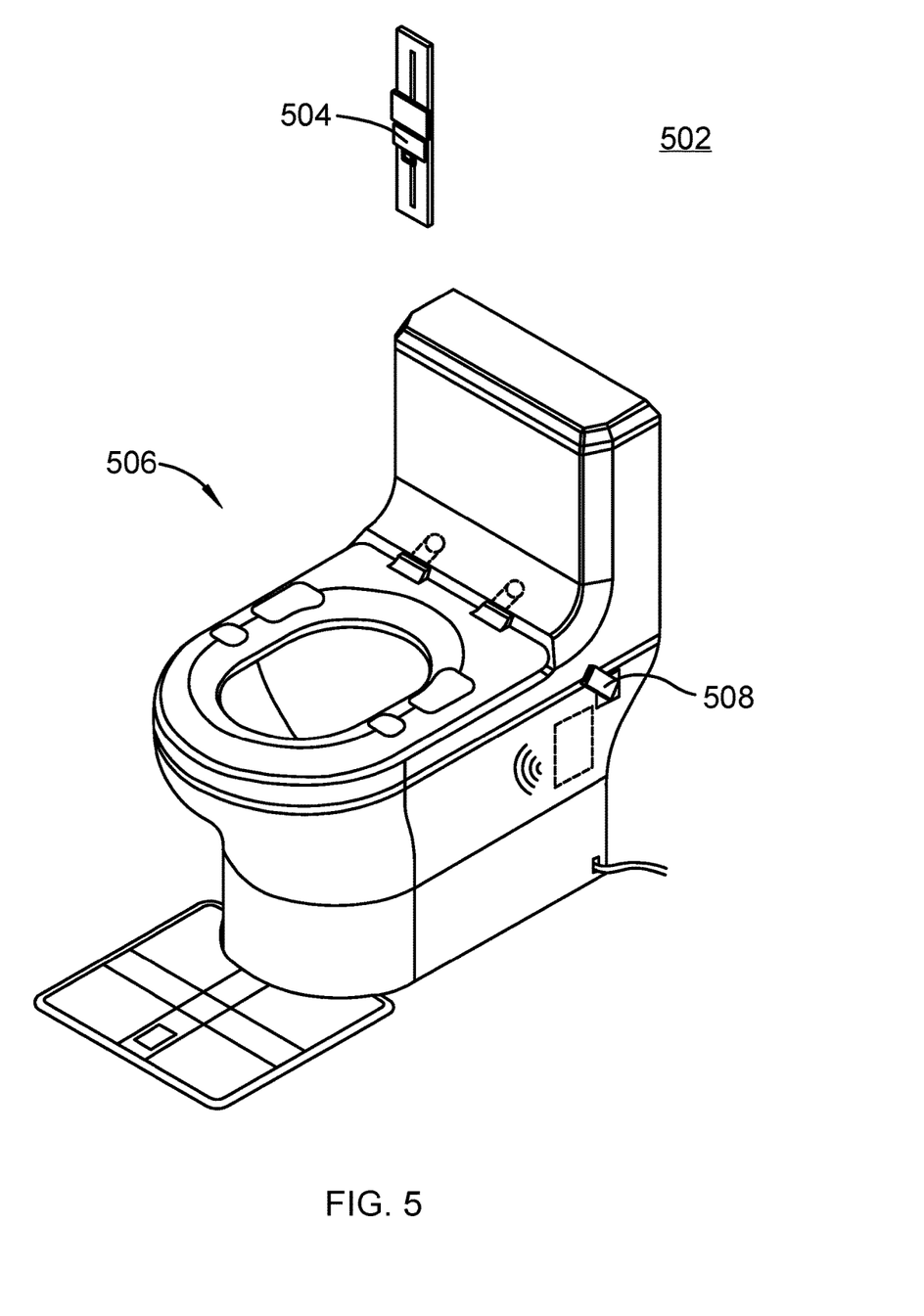
FIG. 5 is an isometric view of a toilet with a diagonal torso belt in accordance with an embodiment of the invention.

FIG. 5 show a similar toilet to FIG. 4 except the torso belt 504 is now located on a bathroom wall 502 along with the height adjustment mechanism. The receiving buckle 508 is shown fixed to a toilet base section. The placement of the receiving buckle 508 allows the torso belt 504 to be extended in a diagonal across a toilet user while the toilet user is sitting on the toilet.

Figure 6:
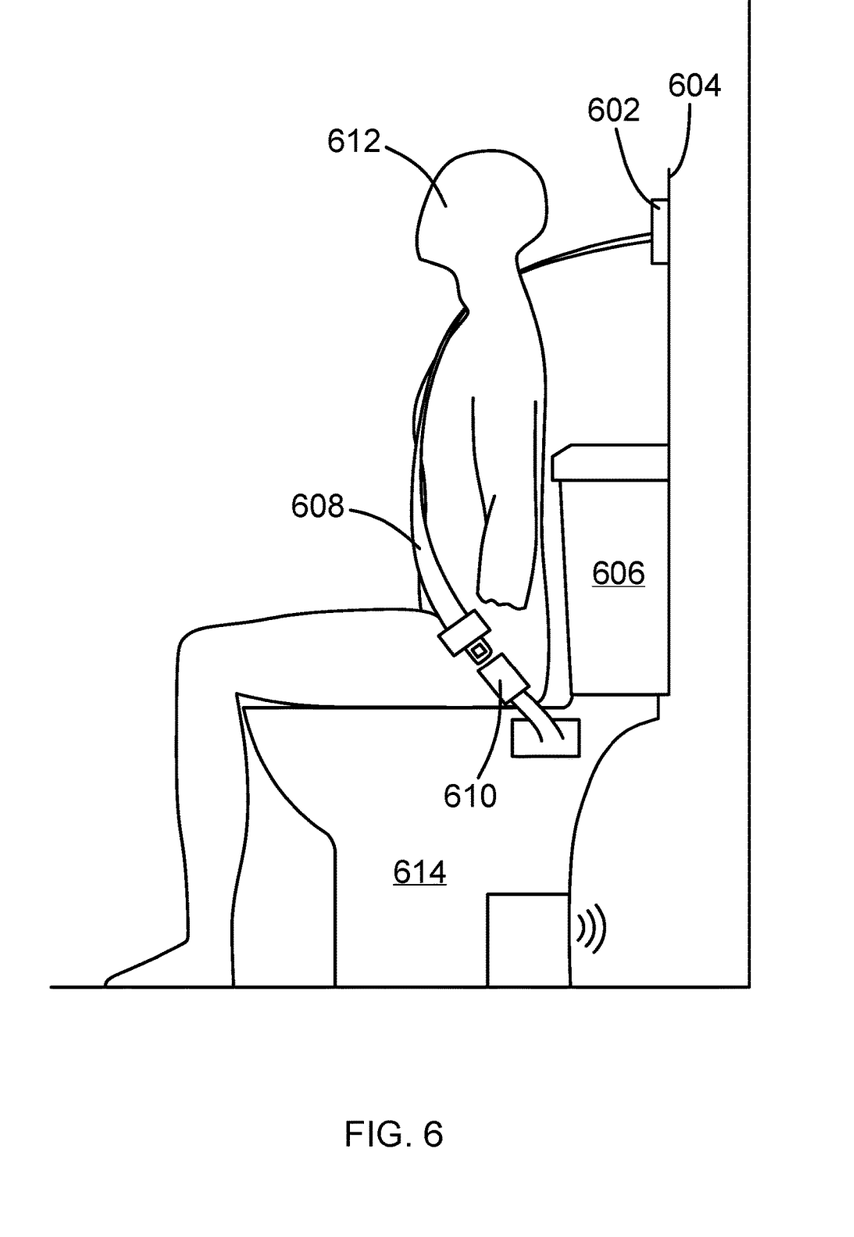
FIG. 6 is a side view of a toilet user sitting on a toilet with a diagonal torso belt in accordance with an embodiment of the invention.

In FIG. 6, a toilet user 612 is sitting on toilet base section 614 with torso belt 608 diagonally extended across the user's torso. Torso belt 608 is connected to a tensioning device 602 which is attached to toilet tank 606. The tensioning device 602 may optionally be attached to a bathroom wall as shown in FIG. 5.

Figure 7:
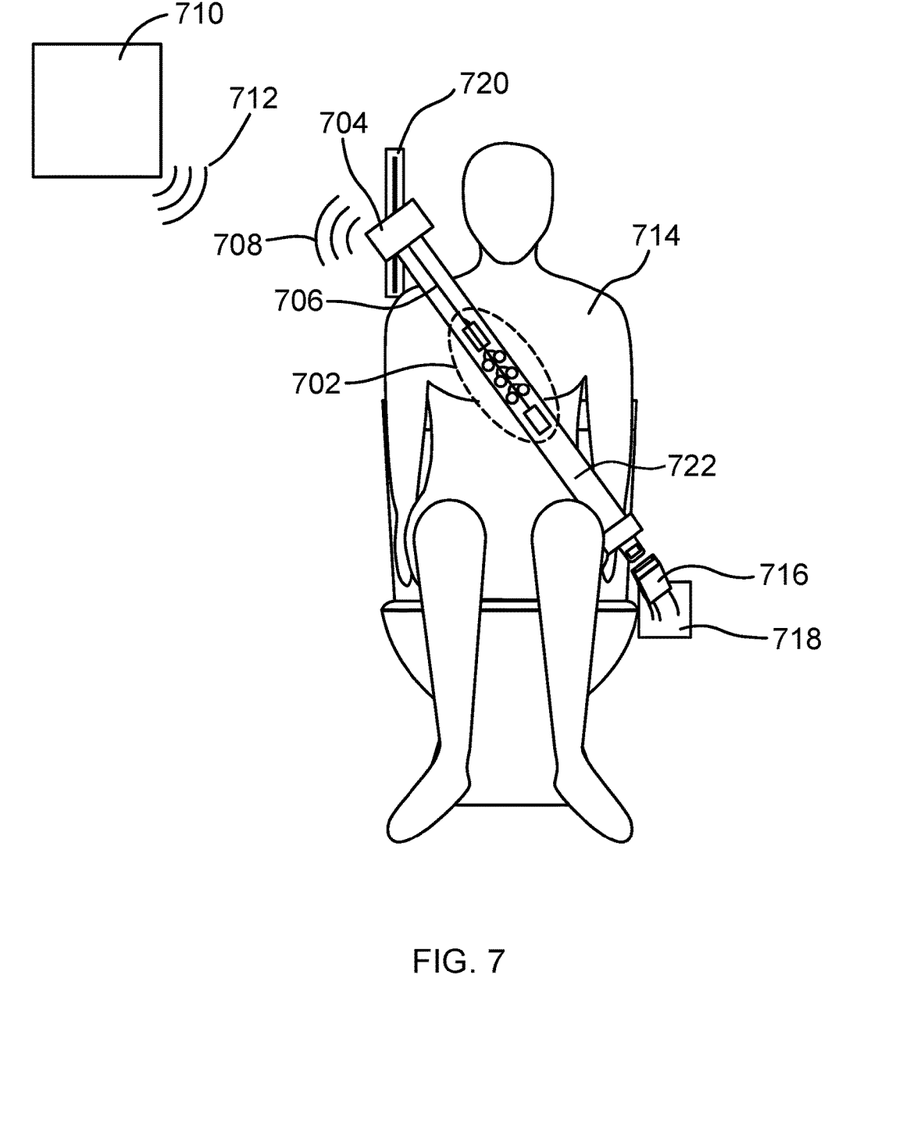
FIG. 7 is a front view of a toilet user sitting on a toilet with a diagonal torso belt in accordance with an embodiment of the invention.

In FIG. 7, a toilet user 714 is using a toilet to eliminate waste by bearing down and pushing the waste out. As the user is bearing down, motion sensors or strain sensors 702 within the torso belt 722 detect send signals indicative of the user bearing down to wireless controller 704. Upon receiving an indication of the user bearing down, the controller starts obtaining ECG readings of the user to monitor the user's heart as stress is applied to the heart from the user bearing down to eliminate waste. Controller 704 may record in memory or transmit to a remote storage device data obtained from sensors 702. The sensors 702 may comprise one or more of: electrode sensors, microphone sensors, acoustic sensors, ultrasound sensors, motion sensors, strain sensors, optical sensors, temperature sensors, electrocardiogram (ECG or EKG) sensors, and/or stethoscope sensors. The sensors may receive data for determining a user's temperature, respirations, heart rate, electrocardiogram, echocardiogram, and stethoscope sounds. A controller may be coupled to the sensors and programed to determine one or more of: a user's temperature, respirations, heart rate, electrocardiogram, echocardiogram, and stethoscope sounds from the data received from the one or more sensors in the torso belt. The sensors 702 may have wires which run along the torso belt or which are imbedded within the torso belt. The wires may connect to a wireless controller located within the toilet or to wireless controller 704. The wireless controller 704 may process and communicate signals 708 obtained from sensors 702 to a remote location such as a server or computer 710. The data may be stored in connection to a user or user profile. The data may be used for health monitoring purposes and may be evaluated by remotely located physicians. A receiving buckle end 716 may be connected to a bathroom wall or to the toilet. The sensors 702 may include transmit receive pairs, transducers, transmitters, electrodes, optical transmitters and receivers, ultrasonic transmitters and receivers, acoustic transmitters and receivers, etc.

Figure 8:
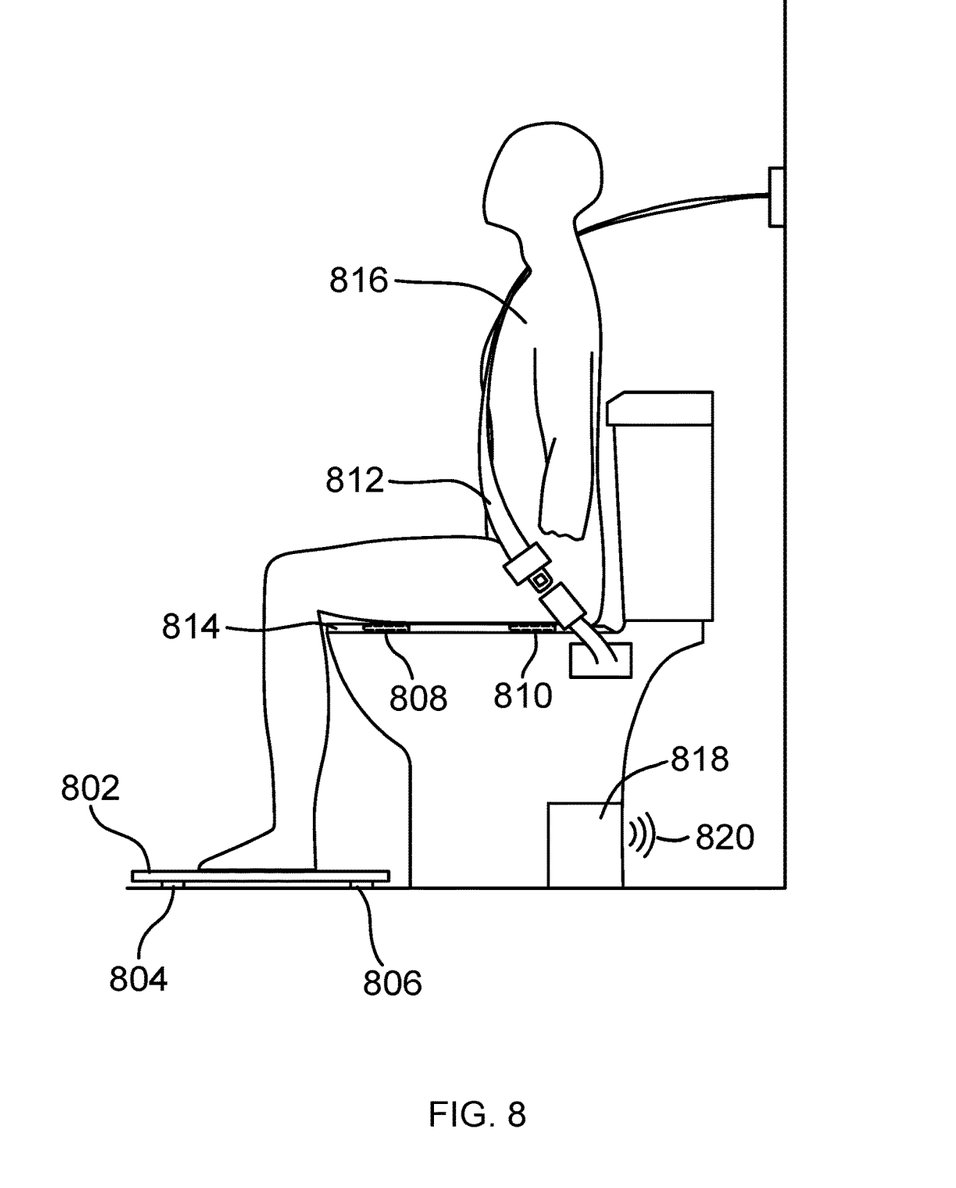
FIG. 8 is a side view of a toilet user sitting on a toilet with a diagonal torso belt in accordance with an embodiment of the invention.

In FIG. 8, a toilet user 816 is positioned on a toilet with torso belt 812 diagonally positioned across the user's torso 816. The user's bottom and thighs are touching sensors 808 and 810 embedded in the toilet seat 814 and the user's feet are touching bio-metric electrodes on the surface 802 of the foot scale. The foot scale contains two or more strain sensors 804 and 806 for determination of a weight of a user using the toilet. The user's weight may be determined in part by strain sensors which are located on or near toilet seat 814 and on or near scale surface 802. A wireless toilet controller 818 may be in wireless or wired communication with toilet seat 814, torso belt 812, and/or foot scale 802. The toilet controller may obtain health measurement data related to a user's health and report the data to an online repository or network data base location. The data may include: bio-impedance electrode sensor data, microphone sensor data, acoustic sensor imaging data, ultrasound imaging sensor data, motion sensor data, strain sensor data, optical sensor data, temperature sensor data, electrocardiogram (ECG or EKG) sensor data, and/or stethoscope noise data.

User health data may be sampled and stored in a remote database. The stored data may be used to create a rolling history and rolling averages of health conditions of a toilet user. Rolling averages of heart rate, temperature, respirations of a user, blood flow, heart rate while eliminating waste, bio-impedance, hydration levels, heart valve function, etc. may be mapped overtime and significant changes to a rolling average may be flagged for review by a physician or automatically sent to the user's doctor. The stored data may be used to determine the amount of exertion a user gave while eliminating waste. This exertion may be correlated with constipation and may be used to detect constipation based heart readings of a user.

The toilet and methods disclosed herein may be embodied in other specific forms without departing from their spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A toilet, comprising
   a user toilet seat, the user toilet seat comprising one or more sensors;
   a torso belt;
   a torso belt tensioner;
   one or more sensors attached to the torso belt, the torso belt configured to extend across a torso of a user while the user is sitting on the toilet;
   wherein the one or more sensors comprise a motion sensor or strain sensor configured to detect and transmit signals indicative of a user bearing down;
   wherein the one or more sensors comprise removable electrodes configured to obtain electrocardiogram measurements indicative of the user bearing down;
   wherein the torso belt tensioner is configured to compress the torso belt against the torso of the user while the user is on the toilet seat with sufficient force to allow the one or more sensors to measure the user of the toilet.

2. The toilet of claim 1, wherein the torso belt comprises one or more electrocardiogram sensors, ultrasonic imaging sensors, or bio-impedance sensors.

3. The toilet of claim 1, wherein the torso belt comprises one or more acoustic imaging sensors.

4. The toilet of claim 1, wherein the torso belt comprises a microphone or a stethoscope.

5. The toilet of claim 1, wherein the torso belt comprises an electrocardiogram sensor, and ultrasonic sensor, and a microphone.

6. The toilet of claim 1, wherein the sufficient force is in the range of about 2. 5 N to about 35 N per linear belt inch.

7. The toilet of claim 1, wherein the tensioner provides a variable force against the torso of the user based upon sensors selected by the user and upon the user's height, weight, sex, and age.

8. The toilet of claim 1 wherein the torso belt further comprises a height adjustment mechanism.

9. The toilet of claim 1, wherein the torso belt further comprises a defibrillator.

10. The toilet of claim 1, wherein the torso belt diagonally extends across a torso of the toilet user.

11. The toilet of claim 1, wherein the torso belt horizontally extends across a torso of the toilet user.

12. The toilet of claim 1, wherein the torso belt comprises wires connecting the one or more sensors to a wireless transceiver.

13. The toilet of claim 1, wherein the torso belt is configured to retract or extend by rolling up or by rolling out.

14. The toilet of claim 1, wherein the torso belt comprises a buckle mechanism that attaches to a base of the toilet or to a tank of the toilet.

15. The toilet of claim 1, wherein the removable electrodes are configured to obtain bio-impedance measurements.

16. The toilet according to claim 15, wherein the removable electrodes are configured to obtain both electrocardiogram measurements and bio-impedance measurements.

17. The toilet of claim 1, wherein the removable electrodes are configured to defibrillate a heart of the toilet user while sitting on the toilet.

18. A toilet comprising:
    a torso belt comprising one or more sensors that are configured to measure a toilet user while the toilet user is using the toilet;
    wherein the one or more sensors comprise a motion sensor or a strain sensor configured to detect signals indicative of a user bearing down;
    wherein the one or more sensors comprise removable electrodes configured to obtain electrocardiogram measurements indicative of the user bearing down; and
    a user toilet seat, the user toilet set comprising one or more sensors.

* * * * *